United States Patent [19]

Pack

[11] 4,446,138

[45] May 1, 1984

[54] METHOD AND COMPOSITION FOR REDUCING WEIGHT

[76] Inventor: Howard M. Pack, 12 Herkimer Rd., Scarsdale, N.Y. 10583

[21] Appl. No.: 347,492

[22] Filed: Feb. 10, 1982

[51] Int. Cl.$^3$ ............................................. A61K 27/00
[52] U.S. Cl. ................................................ 424/248.57
[58] Field of Search ................................... 424/248.57

[56] References Cited

U.S. PATENT DOCUMENTS

| | | | |
|---|---|---|---|
| 3,491,093 | 1/1970 | Pachter et al. | 424/248.57 |
| 3,795,739 | 3/1974 | Birkmayer et al. | 424/274 |
| 3,939,253 | 2/1976 | Bodor et al. | 424/309 |
| 4,035,507 | 7/1977 | Bodor et al. | 424/311 |

OTHER PUBLICATIONS

Chem. Abst. 82, 25910(c) (1975), Shibiaya.
Chem. Abst. 86, 25944(z) (1977), Moore et al.
Rivera–Calimlim et al. "Morphologic and Biochemical Changes in the Gut after Chronic Treatment with L–Dopa" *J. of Pharm. & Exp. Therapeutics*, 184:2 (1973), pp. 440–448.
Gardos et al. "Weight Reduction in Schizophrenics by Molindone" *Amer. J. Psychiatry* 143: Mar. 3, 1977, pp. 302–304.

*Primary Examiner*—Douglas W. Robinson
*Attorney, Agent, or Firm*—Fitch, Even, Tabin & Flannery

[57] ABSTRACT

A method for reducing weight by the administration of L-Dopa or a stabilized form thereof with or without a decarboxylase inhibitor and Molindone wherein Molindone acts as a potentiator to enhance the weight reducing potency of L-Dopa in warm-blooded animals. The synergistic effect of the combination of L-Dopa and Molindone reduces the required dosage of the two drugs to levels which can be tolerated by higher forms of mammals, whereas individually the dosages required to reduce weight in higher mammals is not easily tolerated and may be toxic or lead to undesirable side effects.

8 Claims, No Drawings

METHOD AND COMPOSITION FOR REDUCING WEIGHT

The present invention relates generally to the treatment of obesity by means of the internal administration of pharmaceuticals. More particularly, the invention pertains to the improved administration of L-Dopa with or without a decarboxylase inhibitor plus a potentiator, Molindone, to treat obesity.

BACKGROUND OF THE INVENTION

The health problems associated with the widespread problem of obesity need not be elaborated. A need exists for pharmaceutical treatments which are effective for the treatment of obesity in mammals with a minimum of undesirable side effects. By "obese warm-blooded animal" is meant a human or other mammal which is more than 10 percent overweight as judged by contemporary medical standards. Many treatments have been proposed for obesity. For example, U.S. Pat. No. 3,867,539 to Henkin describes a treatment wherein anorexia is produced by administration of histidine to the obese patient. However, no effective pharmaceutical treatment is believed in widespread use due to a lack of either lasting effectiveness or of undesirable side effects.

DESCRIPTION OF THE PRIOR ART

L-Dopa is the trivial name for the naturally occurring compound L-3, 4-dihydroxyphenylalanine, which is commercially available—its synthesis having been reported in the literature (Yamada et al., *Chem. Pharm. Bull.*, 10:693 (1962)).

The most widely recognized therapeutic use of L-Dopa is in the treatment of Parkinson's disease. The mechanism of L-Dopa in the treatment of this disease is attributed to its presumed role in the correction of an imbalance of dopamine and acetylcholine in the basal ganglia, a biochemical defect associated with Parkinsonism.

L-Dopa has also been used as a treatment of ethanol withdrawal symptoms, as reported in the U.S. Pat. No. 3,995,058 to Hammond et al. The treatment of paralysis agintans with L-Dopa and with mixtures of L-Dopa and benzodiazepines is reported in U.S. Pat. No. 3,984,545 to Frills, Jr. et al. Therapeutic use of L-Dopa in the treatment of depression, sleep production in mice, supranuclear palsy and hepatic coma has also been reported.

It has been reported by Leonor Rivera-Calimlim, et al. in *The Journal of Pharmacology and Experimental Therapeutics*, 184:2 Sept. 18, 1972 that daily administration of L-Dopa causes weight reduction in rats. Weight loss in Parkinson patients treated long term with L-Dopa has also been reported, T Vardi etc. L-Dopa induced weight reduction is believed to be the result of several factors including altered absorptive capacity of the gut, loss of appetite, enhanced lipid metabolism and/or basal metabolism. (There have also been reports showing that L-Dopa induces weight gain).

Molindone hydrochloride is the trivial name of 3-ethyl-6,7 dihydro-2-methyl 5 morpholinomethyl indol-4(5H) one hydrochloride, which is described in U.S. Pat. No. 3,491,093 and is commercially available from Endo Laboratories under the trademark "Moban" and from Abbott Laboratories under the trademark "Lindone".

Molindone has an action which resembles that of major tranquilizers causing reduction of spontaneous locomotion aggressiveness, suppression of a conditional response and antagonism of the bizarre stereotyped behavior and hyperactivity induced by amphetamines. Heretofore, Molindone was prescribed primarily for the treatment of schizophrenia. Recommended human dosages generally range from 15 to 225 mg. per day, although 800 mg. has been administered in one case.

It has been reported by George Gardos and Jonathan Cole in *The American Journal of Psychiatry* 134:3, March 1977, that Molindone has caused weight loss in schizophrenics. A usual clinical course in schizophrenics is for improvement of patient's clinical condition to be accompanied by weight gain and deterioration to be accompanied by a corresponding weight loss. Gardos and Cole reported that when schizophrenic patients were administered Molindone, improvements of their clinical conditions were achieved without accompanying weight gain and in most cases by significant weight loss. There are also reports showing weight gain and improved appetite in Molindone treated patients, e.g., Sugarmann & Herrmann, Chem. Pharm. Ther. 8:261–65, 1967.

SUMMARY OF THE INVENTION

It has been found that simultaneous administration of L-Dopa, with or without a decarboxylase inhibitor, plus Molindone hydrochloride results in weight loss substantially in excess of that which would be expected by the additive effects of the drugs individually and that the combination of L-Dopa and Molindone is a unique combination demonstrably superior as an anti-obesity composition to doses of either drug alone. The effective dosage of the two drugs in combination is reduced to levels that can be tolerated without the undesirable side effects of the higher dosage required if the drugs were administered singly.

DETAILED DESCRIPTION OF THE INVENTION

Molindone and L-Dopa, each of which have previously been known to cause weight reduction in warm-blooded animals, have been found to have a synergistic effect when used in combination with each other. It has been found that Molindone functions as a potentiator to significantly increase the weight reducing functions of L-Dopa or L-Dopa compositions. Although the term "L-Dopa" is used throughout the application, it should be construed to include other known compounds in chemically equivalent amounts which are converted in the body to L-Dopa, such as known precursors, i.e., pro-L-Dopa.

Dopamine, which is formed by the decarboxylation of L-Dopa, is the chemical which actually associates with the brain receptors to produce the pharmaceutical effects associated with L-Dopa. The amount of dopamine available to the brain is generally provided by the L-Dopa which decarboxylizes within the brain. The action of the Molindone potentiates the effect of the dopamine in the brain or peripherally.

Accordingly, the L-Dopa is preferably used in combination with a stabilizer, such as an L-Dopa decarboxylase inhibitor, to prevent premature metabolism and breakdown of the L-Dopa which may occur in the gut mucosa or elsewhere before reaching the brain. The level of L-Dopa required is reduced if the L-Dopa is administered in stabilized form, and it is known to stabilize L-Dopa with an L-Dopa decarboxylase inhibitor. Stabilized compositions of L-Dopa may contain an L-Dopa decarboxylase inhibitor in amounts of from about 6% to about 100% and preferably between 10% and 20% by weight of the L-Dopa. Stabilized compositions of L-Dopa may be from about 4 to about 10 times as effective as L-Dopa in providing the precursor L-Dopa which metabolizes dopamine in the brain.

Examples of suitable L-Dopa decarboxylase inhibitors include N'-(D,L-seryl)-N"-3,3,5-(trihydroxybenzyl)-hydrazine (benzerside), the hydrochloride or maleate salt thereof and α-methyl-dopahydrazine (carbidopa). Commercially available stabilized L-Dopa products include an L-Dopa composition sold under the trademark "Sinemet", available from Merck, Sharpe and Dome, Inc., which contains ten parts L-Dopa to one or two parts carbidopa by weight. A similar product is available under the trademark "Madopar" from Hoffman Laroche, Inc., which contains four parts of L-Dopa to one part of benzerside.

The daily dosage of L-Dopa, decarboxylase and Molindone (stabilized form) which is effective may be varied within a relatively wide range and, to some extent, is dependent upon the requirements of the individual subject or species. In general, in animals, the daily administration of from about 0.005 milligrams of L-Dopa per gram of body weight to about 1 milligram per gram of body weight plus between 0.5% to 50% Molindone to L-Dopa by weight is effective, dependent always on the species and the individual. If administered on a dosage per weight of food basis, L-Dopa is administered at between 2 mgs and 400 mgs per gram of food along with the Molindone and preferably the decarboxylase. The dosage of a simple L-Dopa composition and Molindone without a decarboxylase inhibitor (unstabilized form) will be administered in amounts to generally provide about 4 times as much as the L-Dopa in a stabilized L-Dopa composition with up to 50% Molindone by weight.

While it is useful to define dosages in terms of milligrams of drug per gram of body weight for lower animals, for the treatment of obesity in humans, it is more useful to speak of a particular dosage administered per day. For an adult human, the effective daily dosage of non-stabilized L-Dopa to effect weight loss is between about 0.5 to about 20 grams per day, plus a proportionate amount of Molindone between 0.5 and 50% of the L-Dopa. For a stabilized form of L-Dopa the dosage is between about 0.25 to about 4 grams per day. The percentage of Molindone is between 1.0 and 50% of the L-Dopa.

It has been found that when Molindone in a proportion of 0.5 to 50% of the L-Dopa is administered with L-Dopa or an L-Dopa composition, warm-blooded animals experience a weight loss significantly greater than would be expected from the weight reducing effects of either drug or drug form alone. While there are some reports in the literature which show that when used alone, Molindone and L-Dopa are each known to cause weight reductions in warm-blooded animals, there are also reports to the contrary. However, the synergistic effect of the two compounds is unexpected.

To potentiate the weight reducing properties of L-Dopa, an effective amount of Molindone is administered daily along with, perferably simultaneously with, an effective daily dosage of L-Dopa or an L-Dopa composition.

The amount of L-Dopa in stabilized or unstabilized form plus the percentage by weight of Molindone is determined according to the amounts that reach the brain. It has been found that using the stabilized form plus the Molindone is advantageous since it permits the use of less L-Dopa and Molindone to achieve the desired weight loss. The large doses of these drugs used singly needed to effect weight reduction in higher mammals lead to the creation of undesirable side effects while the smaller doses of the two drugs in combination causes less undesirable side effects.

EXAMPLE 1

In order to demonstrate the efficacy of Molindone as a potentiator of the weight reducing properties of Sinemet, genetically obese Zucker rats are provided with ad lib access to food (as much food as they choose to eat) which is admixed with various proportions of Sinemet (1 part Carbidopa to 10 parts by weight of L-Dopa) and/or Molindone. The rats are allowed ad lib access to food in order to best measure the combined appetite and metabolic weight reducing effects. The subjects for this invention are Zucker rats which are homozygous for a form of obesity which is carried as a recessive gene. When allowed ad lib access to normal rat feed, the Zucker rats become hyperphagic and invariably gain weight. Excessive weight is added to the Zucker rat by the preferential utilization of dietary amino acids for fat synthesis and is a constant characteristic of the genotype. With advancing age, the Zucker rat becomes sedentary and grossly obese.

Male obese Zucker rats are weight matched into groups of four or five animals each. The rats are individually caged, and all animals are allowed ad lib access to a powdered rat feed and water. Throughout the experiment the proportions of Molindone and/or Sinemet admixed with each rat's food is kept constant.

A conrol group (Group 1) is allowed ad lib access to unadulterated powdered rat feed to measure the normal food intake and weight gain to be expected from Zucker rats which are not administered weight reducing drugs.

Groups 2 and 7 are included to demonstrate the efficacy of L-Dopa as a weight reducing compound. Group 2 receives 8.8 mgs. of Sinement (8 mgs. L-Dopa and 0.8 mg. carbidopa) per gram of feed. Group 7 receives more than triple the proportion of Sinemet per gram of food as Group 2, i.e., 27.5 mg Sinemet per gram of food, to demonstrate the effects of exaggerated amounts of Sinemet.

Groups 8 and 9 are included to illustrate the efficacy of Molindone as a weight reducing compound. Group 8 receives 0.55 mg Molindone per gm. of food. Group 9 receives 1.1 mg Molindone per gm. of food to demonstrate the effects of exaggerated amounts of Molindone.

In Groups 3-6, Molindone and L-Dopa are simultaneously administered to the rats. All groups received 8.8 mg of Sinemet per gm. of food intake (as does Group 2). Groups 3, 4, 5 and 6, respectively, receive Molindone at Sinemet to Molindone ratios of 48:1, 32:1, 24:1 and 16:1 by weight. Group 6 which receives Molindone at a Sinemet to Molindone ratio of 16:1 receives an amount of Molindone per gram of food identical to that of Group 8.

The food intake of each animal is measured on a daily basis. The animals are weighed every 4 days.

The experiment is carried out over a period of 60 days. At the end of 60 days the results are achieved as set forth in Table 1 below.

TABLE 1
Comparison of Sinemet, Molindone and food intake with weight change

| Group | Mg Sinemet (10 parts L-Dopa to 1 part Carbidopa) per gm of Food | Sinemet mg. Approx. (Average per rat per day) | Molindone (mg/gm of Food) | Mg Molindone per gram of food | Food gm. (Average per rat per day) | Wt. Change as % of Orig. Wt. (Collective Wt. change of group at end of 60 days) |
|---|---|---|---|---|---|---|
| 1 | 0 | 0 | 0 | 0 | 27.6 | +12% |
| 2 | 8.8 | 195 | 0 | 0 | 22.1 | −25% |
| 3 | 8.8 | 184 | 0.18 | 3.9 | 20.9 | −32% |
| 4 | 8.8 | 173 | 0.27 | 5.5 | 19.6 | −38% |
| 5 | 8.8 | 125 | 0.37 | 5.3 | 14.2 | −49% |
| 6 | 8.8 | 109 | 0.55 | 6.9 | 12.3 | −54% |
| 7 | 27.5 | 371 | 0 | 0 | 13.5 | −46% |
| 8 | 0 | 0 | 0.55 | 13.4 | 24.3 | −15% |
| 9 | 0 | 0 | 1.10 | 23.2 | 21.1 | −24% |

The rats of Group 1, as is expected of genetically obese Zucker rats, gain weight steadily. Groups 2 and 7 confirm the weight reducing properties of L-Dopa. Increased dosage of L-Dopa (Group 7) causes corresponding increased weight loss.

Groups 8 and 9 confirm the weight reducing properties of Molindone. Increased dosage of Molindone (Group 9) causes increased weight loss.

It may be seen, when comparing Groups 3 through 6 with Group 2, all of which are administered Sinemet in identical proportions per gram of food, that simultaneous administration of Molindone potentiates the weight reducing properties of a stabilized L-Dopa composition. Within the range used herein, the potentiating effect of Molindone on the weight reducing properties of a stabilized L-Dopa composition increases with increased Molindone concentrations as demonstrated by the progression of increased weight loss of Groups 3 through 6.

Particularly significant is the fact that when rats are concurrently fed Molindone and a stabilized L-Dopa composition, the weight loss is greater than that which would be expected from the additive effects of L-Dopa and Molindone. On a weight per gram of food basis, Group 6 is administered a dosage of Sinemet equal to that of Group 2 (no Molindone) and a dosage of Molindone equal to that of Group 8 (no Sinemet). The combined weight loss of Group 2 (25%) and Group 8 (15%) is (40%) which is significantly less than the weight loss (54%) achieved by Group 6. The synergistic effect of the Molindone-stabilized L-Dopa composition is even more dramatically illustrated by comparing the weight loss of Group 6 with the combined weight losses of Groups 2 and 8 in view of the average daily doses of Sinemet and Molindone actually ingested. Due to decreased daily intake of food by Group 6, Group 6 actually intakes about one half the Sinemet of Group 2 and about one half the Molindone of Group 8, and yet Group 6 loses more combined weight than Groups 2 and 8 together. It is therefore demonstrated that the combination of L-Dopa, i.e., Sinemet, and Molindone, has a synergistic effect. The drugs used in combination result in a weight loss significantly greater than that which would be calculated by adding the weight losses which are expected from comparable doses of the individual drugs.

A comparison of either Group 5 or Group 6 with Group 7 demonstrates that adding Molindone to a stabilized L-Dopa composition in ratios of 1:24 and 1:16, respectively, is at least as effective in reducing weight as is tripling the dosage of the L-Dopa composition on a weight per gram of food basis. Approximately the same results may be observed by comparing the average daily intake of Sinemet of Groups 5 or 6 with Group 7.

EXAMPLE 2

To further illustrate the synergistic effect that Molindone has on L-Dopa, another experiment was performed. Lean Zucker rats were given 3.3 milligrams of Sinemet per 1000 grams of food. This low dose did not reduce body weight. At the end of 36 days, the rats on this dosage had gained 1.2% of their original body weight. Another comparable group of lean Zucker rats was placed on the same dosage of Sinemet, but 0.45 milligram or less than half a milligram of Molindone was added to the food. At the end of 36 days, this group had lost 15.8% of their original body weight. The importance of this potentiating effect is that it permits L-Dopa dosages in the range already approved for Parkinson patients whereas, used alone, L-Dopa would greatly exceed the permitted human dosage in order to be effective.

Molindone and stabilized L-Dopa is thereby shown to potentiate the weight reducing properties of L-Dopa in mammals.

EXAMPLE 3

A further demonstration of the potentiating effect of Molindone is proven in an experiment with Zucker lean rats whereby a composition of 2 mg. of L-Dopa, 0.2 mg. of carbidopa and 0.675 mg. of Molindone per gram of food is added to the powdered chow. Since a dosage of 3 mg. of L-Dopa, 0.3 mg. of carbidopa per gram of food does not cause weight loss, clearly a 2 mg./0.2 mg. L-Dopa/carbidopa dosage will not. However, when the 0.675 mg. of Molindone per gram of food is added, after only eight days the weight change is −16.18%. Thus a high weight percent of Molindone to a small dosage of L-Dopa/carbidopa is clearly shown to have a very strong potentiating effect.

EXAMPLE 4

To further test the efficacy of the two drug combination in higher mammals, an experiment was performed on Bonnet Macaque monkeys. For a period of 76 days, the monkeys were fed a diet of bread and peanut butter. The groups which received the drug had it mashed in the peanut butter. The control group received plain peanut butter sandwiches. Four groups were established: 4 Obese Males, 4 Obese Females, 4 Lean Males/Females and 5 Lean Male/Female controls. The results are summarized in the tabulation below:

|  | No. | Average Drug Intake | | | Weight (Lbs.) Day 1 | Weight Day 76 | % Change |
|---|---|---|---|---|---|---|---|
|  |  | L-Dopa | Decarb-oxylase | Molindone |  |  |  |
| Obese Males | 4 | 628 | 126 | 94 | 29.81 | 26.89 | −9.8% |
| Obese Females | 4 | 550 | 110 | 83 | 21.5 | 19.52 | −9.2% |
| Lean Males/Females | 4 | 462 | 92 | 69 | 12.99 | 12.27 | −5.5% |
| Lean controls Males/Females | 5 | NO DRUG | | | 17.9 | 17.56 | −1.9% |

The results clearly demonstrate the efficacy of the two-drug combination on higher mammals. The median amount of ingested drug in the animals receiving the drug was about 550 mg. of Sinemet plus about 82.5 mg. of Molindone. This amount translated to human dosages is within the safe effective range.

L-Dopa, Molindone compositions according to the present invention are generally administered orally, subcutaneously, intramuscularly, nasally, interperitoneally, intravenously, via any mucus membrane or by any other method commonly used to administer pharmaceutical compositions.

While the whole invention has been described by specific examples, modifications obvious to one skilled in the art may be made without departing from the teaching of the instant invention which is limited only by the following claims.

What is claimed:

1. A composition for use in the treatment of obesity comprising L-Dopa, a decarboxylase inhibitor in amounts of between about 6% and about 100% by weight of said L-Dopa, and Molindone in amounts of between 1.0 and 50 weight percent of said L-Dopa.

2. A composition in accordance with claim 1 wherein said decarboxylase inhibitor is selected from the group consisting of carbidopa and benzerside.

3. A method for treatment of obese warm-blooded animals comprising concurrently administering L-dopa at a daily level of from about 0.01 milligram to about 1 milligram per gram of body weight and Molindone at a daily level of from about 1.0 to about 50 weight percent of said L-dopa, and a decarboxylase inhibitor at a daily level of from about 6 to about 100 weight percent of said L-dopa, whereby weight loss is effected in the animal.

4. A method in accordance with claim 3 wherein said warm-blooded animal is human and between about 0.25 and about 4.0 grams of said L-Dopa are administered daily.

5. A method in accordance with claim 3 wherein said decarboxylase inhibitor is selected from the group consisting of carbidopa and benzerside.

6. A method for treatment of obese warm-blooded animals comprising concurrently administering L-dopa at a daily level of from about 0.01 milligram to about 0.5 milligram per gram of body weight, Molindone at a daily level of from about 1.0 to about 50 weight percent of said L-dopa and carbidopa at a daily level of from about 6 to about 100 weight percent of said L-dopa, whereby weight loss is effected in the animal.

7. A method in accordance with claim 6 wherein said warm-blooded animal is human and between about 0.25 and about 4.0 grams of said L-dopa are administered daily.

8. A composition for use in the treatment of obesity comprising L-dopa, carbidopa in amounts of between about 6 and about 100 weight percent of said L-dopa, and Molindone in amounts of between 1.0 and 50 weight percent of said L-dopa.

* * * * *

UNITED STATES PATENT AND TRADEMARK OFFICE
CERTIFICATE OF CORRECTION

PATENT NO. : 4,446,138
DATED : May 1, 1984
INVENTOR(S) : Howard M. Pack

It is certified that error appears in the above-identified patent and that said Letters Patent is hereby corrected as shown below:

Column 4, line 38, change "conrol" to --control--.

Column 5, lines 5-7, change "Molindone (mg/gm of food)" to --Mg Molindone per gm of food--.

Column 5, lines 4-7, change "Mg Molindone per gram of food" to --Molindone mg. Approx. (Average per rat per day)--.

Signed and Sealed this

Second Day of October 1984

[SEAL]

Attest:

GERALD J. MOSSINGHOFF

Attesting Officer

Commissioner of Patents and Trademarks